US00PP08220P

United States Patent [19]

Simchock

[11] Patent Number: Plant 8,220

[45] Date of Patent: May 4, 1993

[54] DOUBLE FLOWERING VARIEGATED IMPATIENS "ORANGE DELITE"

[76] Inventor: Daniel Simchock, 54 Green Meadow Ct., Deer Park, N.Y. 11729

[21] Appl. No.: 793,097

[22] Filed: Nov. 15, 1991

[51] Int. Cl.[5] ..... A01H 5/00
[52] U.S. Cl. ..... Plt./87.6
[58] Field of Search ..... Plt./87.6

[56] References Cited

U.S. PATENT DOCUMENTS

P.P. 7,130 11/1988 Simchock ..... Plt. 87.6
P.P. 7,690 10/1991 Cole ..... Plt. 87.6

*Primary Examiner*—James R. Feyrer
*Attorney, Agent, or Firm*—Frank B. Robb

[57] ABSTRACT

An impatiens plant which is a derivative of the variety known as "Duet" found as a sport in a planting of the variety "Dapper Dan" (U.S. Plant Pat. No. 7,130) where the double deep red flowers are contrasted with foliage which is the usual green of the impatiens leaves, having a variegated border in which the leaf variegation pattern is not uniform in at least two mesophyll layers of leaf tissue rendering the appearance as being layered, the color being of yellowish white and as a border of varying widths. The leaves appear to be substantially the same shape as the variety "Dapper Dan". The overall color of the flowers is noticeable as being substantially more orange than that variety, when the flowers are compared with those of U.S. Plant Pat. No. 7,130.

1 Drawing Sheet

BACKGROUND OF THE INVENTION

This invention relates to a new and distinct variety of impatiens plant which resembles the parent Dapper Dan but has some outstanding differences in that while its foliage is variegated as the parent, the color of the flowers is considerably more orange in overall appearance.

The plant of the instant variety was discovered in my greenhouse in Brentwood, N.Y., as a color sport in a clonal population of the parent plant Dapper Dan. This plant was noticed because of the flower color and its distinctly orange coloration rather than red as in Dapper Dan and not found in any other specimen of the parent variety that I have observed.

It therefore differs from the pollen parent of Dapper Dan which is "Duet" a pink white flower producer.

Since the description of my new variety in most respects follows that of the variety "Dapper Dan" (U.S. Plant Pat. No. 7,130) except for the flower color, that description is changed only as it relates to differences, the variety "Dapper Dan" being distinguishable quite readily when viewed in association with the instant variety which I have chosen to designate for commercial purposes as "Orange Delite".

As previously suggested, the particular difference of color is most noticeable when my new variety is grown in association with the parent variety "Dapper Dan" and is therefore readily distinguishable.

I have caused my new variety "Orange Delite" to be asexually reproduced by stem cuttings at Brentwood, N.Y., and found that it retains the characteristics which make it distinctive through successive generations.

The description may be emphasized by pointing out that the flower buds are borne several to each stem and may occur in clusters at nodes. The buds of each cluster are of uneven maturity and normally only one open flower is presented from a cluster at a time.

While growth of the vareity indoors is not exactly regular, it is normally an annual in outdoor use as the plant is susceptible to frost.

The color designations which I have referred to in the drawing attached hereto, which drawing is representative of a plant of my new variety, discloses the orange coloration, the colors however being as near the colors of the actual plant as is possible to reproduce them by photograph processes as used herein. It is recognizable that without comparison side by side, it is difficult perhaps to distinguish the plants but when that side by side comparison is made, the differences are readily recognizable and quite distinct.

A detailed description which assists in identifying this new plant is set forth hereafter and summarized in the claim set forth at the end thereof.

While the description herein is particularly related to a color chart of Munsell, the instant description as far as the orange color is concerned is derived from the Munsell Limit Color Cascade in contrast to the other and previously used color designations which are applicable herein as being related to and the same as the parent plant of which this variety is a sport.

As seen in the drawing attached hereto a plant of my new variety discloses the color of the flowers and illustrates the form thereof.

Parentage: Sport of variety "Dapper Dan".
Propagation: By cutting.

FLOWER

Borne: Several to stem; regular clusters; and normal long stems.
Quantity of bloom: Moderate; outdoors; in greenhouse.
Continuity: One season; annual by nature.
Bud:

*Size.*—Medium.
*Form.*—Medium.
*Color.*—Pink to white then opens to orange flower. (Orange #36-10).
*Calyx.*—Color — White.
*Peduncle.*—Medium long; medium heavy and smooth. Light green in color.
*Pedicels.*—1½" to 2" across in length. Bud opens well and not affected by adverse conditions.

*Petalage.*—Many under normal conditions. Variations — Variegated leaves; same as parent "Dapper Dan". Discoloration — Green leaf with white yellow variegation.

Petals: Thin and not affected by wet or hot weather. Oval in form and no fragrance. Long lasting quality on the plant.

No reproductive organs: Plant is sterile. Both pistils and stamens are absent and appear to be replaced by additional petals to render a fully double flower. Reproduction has been effected solely by tissue culture.

PLANT

Form: Variegated leaf; double flowering impatiens.

Growth: Vigorous.

Foliage:

*Size.*—Medium.

*Quantity.*—Abundant to normal.

*Color.*—New foliage — Upper side — Moderate olive green 5GY4/3. Variegation — Border — brilliant green yellow 2.5GY9/8. Under side — Inside — Moderate olive green 5GY5/6. Variegation — Border — brilliant green yellow 2.5GY9/8. Old foliage — Upper side — Inside — Moderate olive green 5GY4/3. Varigation — Border — White than 10Y9.9. Under side — Inside — Moderate olive green 5GY4/3. Variegation — Border — White than 10Y9/9.

*Shape.*—Oval pointed.

*Texture.*—Upper and under side smooth.

*Margin.*—Shape — Basically thin line around leaf, some more to center than others.

Not prone to any known diseases.

I claim:

1. A new and distinct variety of impatiens plant, substantially as shown and described, characterized particularly as to novelty by the orange color of the flowers with the foliage having borders of leaves of yellowish white coloration which provide for variegation, the borders being of relatively varying widths from leaf to leaf, the primary distinction residing in the orange coloration as heretofore set forth in contrast to the much more red impatiens "Duet".

* * * * *

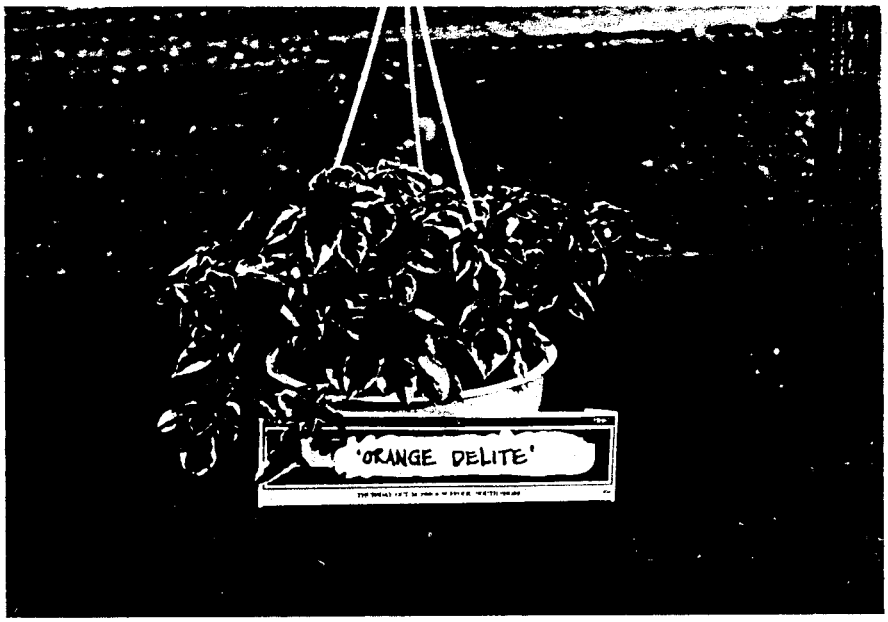
'ORANGE DELITE'